US009375251B2

(12) United States Patent
Lieber et al.

(10) Patent No.: US 9,375,251 B2
(45) Date of Patent: *Jun. 28, 2016

(54) APPARATUS AND METHOD FOR MONITORING EARLY FORMATION OF STEAM POP DURING ABLATION

(71) Applicant: BIOSENSE WEBSTER, INC., Diamond Bar, CA (US)

(72) Inventors: Chad Allen Lieber, Rolla, MO (US); Ariel Garcia, Duarte, CA (US); Shiva Sharareh, Laguna Niguel, CA (US)

(73) Assignee: BIOSENSE WEBSTER, INC., Diamond Bar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/137,681

(22) Filed: Dec. 20, 2013

(65) Prior Publication Data
US 2014/0243812 A1 Aug. 28, 2014

Related U.S. Application Data

(63) Continuation of application No. 13/434,554, filed on Mar. 29, 2012, now Pat. No. 8,641,706, which is a continuation of application No. 11/552,075, filed on Oct. 23, 2006, now Pat. No. 8,147,484.

(51) Int. Cl.
*A61B 18/12* (2006.01)
*A61B 5/00* (2006.01)
(Continued)

(52) U.S. Cl.
CPC ........... *A61B 18/1233* (2013.01); *A61B 5/0084* (2013.01); *A61B 18/1492* (2013.01); *A61B 2017/00061* (2013.01); *A61B 2018/00577* (2013.01); *A61B 2018/00666* (2013.01)

(58) Field of Classification Search
CPC .............. A61B 5/0071; A61B 5/0075; A61B 2018/00636; A61B 2018/00642; A61B 2018/00684; A61B 2018/0069; A61B 2018/00702; A61B 2018/00708; A61B 2018/00904
See application file for complete search history.

(56) References Cited

U.S. PATENT DOCUMENTS 5,464,433 A 11/1995 White et al.
6,127,574 A 10/2000 Howard et al.
(Continued)

FOREIGN PATENT DOCUMENTS

WO  WO 2004/028353 A2  4/2004
WO  WO 2006/055733 A1  5/2006

OTHER PUBLICATIONS

Yokoyama, Katsuaki et al., *Comparison of Electrode Coiling Between Closed Loop and Open Irrigation in Radiofrequency Lesion Depth, Thrombus and Steam POP*, Heart Rhythm, vol. 2, No. 5, Supplement 2005, S74-S75, 2 pages.

(Continued)

*Primary Examiner* — Ronald Hupczey, Jr.
(74) *Attorney, Agent, or Firm* — Lewis Roca Rothgerber Christie LLP

(57) ABSTRACT

A system for measuring real-time tissue reflection spectral characteristics during ablation includes a catheter for collecting light reflected from tissue undergoing ablation, a detection component for separating constituent wavelengths of the collected light, a quantification apparatus for generating measured light intensity data of the collected light, and a processor for analyzing the data in relation to time. A method for monitoring formation of steam pop during ablation includes delivering light to tissue, delivering ablative energy to the tissue, measuring the reflectance spectral intensity of the tissue, and observing whether the measured reflectance spectral instensity (MRSI) initially increases in a specified time period followed by a decrease at a specified rate. If the MRSI does not decrease, delivery of ablation energy continues. If the MRSI decreases within the specified time at the specified rate, formation of a steam pocket is inferred and delivery of ablative energy is decreased or discontinued.

14 Claims, 6 Drawing Sheets

(51) Int. Cl.
*A61B 18/14* (2006.01)
*A61B 18/00* (2006.01)
*A61B 17/00* (2006.01)

(56) References Cited

U.S. PATENT DOCUMENTS

| | | |
|---|---|---|
| 6,217,574 B1 | 4/2001 | Webster |
| 7,662,152 B2 | 2/2010 | Sharareh et al. |
| 8,147,484 B2 * | 4/2012 | Lieber et al. ............ 606/32 |
| 8,641,706 B2 * | 2/2014 | Lieber et al. ............ 606/34 |
| 2004/0039378 A1 | 2/2004 | Lin |
| 2006/0111697 A1 | 5/2006 | Brinkmann et al. |
| 2006/0122587 A1 | 6/2006 | Sharareh |
| 2006/0229515 A1 | 10/2006 | Sharareh et al. |
| 2009/0005768 A1 | 1/2009 | Sharareh et al. |

OTHER PUBLICATIONS

Sharareh, Shiva et al., U.S. Appl. No. 11/281,853, *Method for real Time Evaluation of Tissue Ablation*, filed Nov. 17, 2005, 25 pages.
International Search Report dated Feb. 19, 2008 issued in International Application No. PCT/US2007/082243, 7 pages.

* cited by examiner

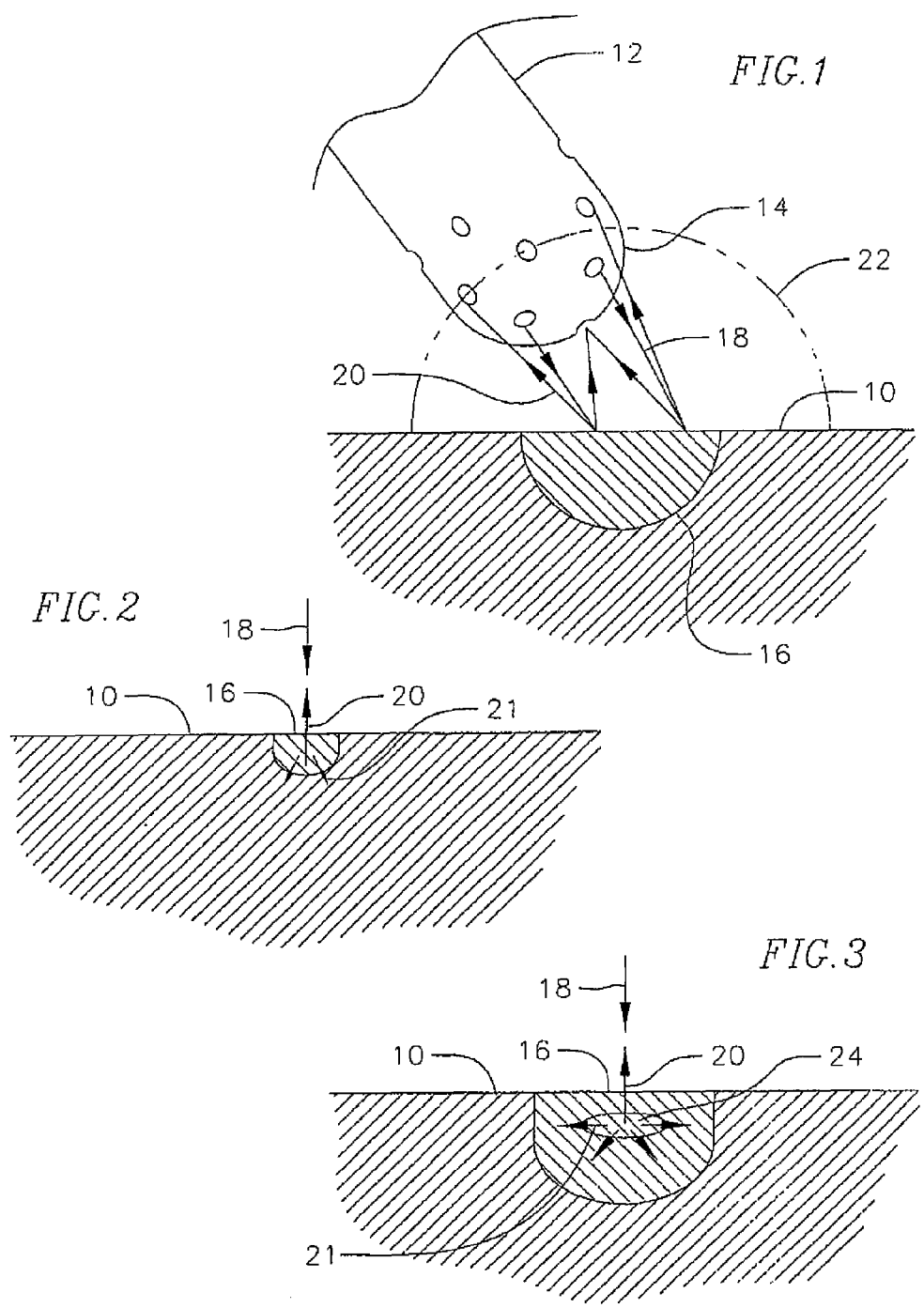

APPARATUS AND METHOD FOR MONITORING EARLY FORMATION OF STEAM POP DURING ABLATION

CROSS-REFERENCE TO RELATED APPLICATION(S)

This application is a continuation of and claims priority to and the benefit of U.S. application Ser. No. 13/434,554 filed Mar. 29, 2012, which is a continuation of U.S. application Ser. No. 11/552,075, filed Oct. 23, 2006, which issued as U.S. Pat. No. 8,147,484 on Apr. 3, 2012, the entire contents of all which are incorporated herein by reference.

FIELD OF THE INVENTION

The present invention relates to ablation catheters, and in particular to ablation catheters with optical monitoring of tissue for predicting steam pops.

BACKGROUND

For certain types of minimally invasive medical procedures, real time information regarding the condition of the treatment site within the body is unavailable. This lack of information inhibits the clinician when employing catheter to perform a procedure. An example of such procedures is tumor and disease treatment in the liver and prostate. Yet another example of such a procedure is surgical ablation used to treat atrial fibrillation. This condition in the heart causes abnormal electrical signals, known as cardiac arrhythmias, to be generated in the endocardial tissue resulting in irregular beating of the heart.

The most frequent cause of cardiac arrhythmias is an abnormal routing of electricity through the cardiac tissue. In general, most arrhythmias are treated by ablating suspected centers of this electrical misfiring, thereby causing these centers to become inactive. Successful treatment, then, depends on the location of the ablation within the heart as well as the lesion itself. For example, when treating atrial fibrillation, an ablation catheter is maneuvered into the right or left atrium where it is used to create ablation lesions in the heart. These lesions are intended to stop the irregular beating of the heart by creating non-conductive barriers between regions of the atria that halt passage through the heart of the abnormal electrical activity.

The lesion should be created such that electrical conductivity is halted in the localized region (transmurality), but care should be taken to prevent ablating adjacent tissues. Furthermore, the ablation process can also cause undesirable charring of the tissue and localized coagulation, and can evaporate water in the blood and tissue leading to steam pops. The damage caused by steam pops can cause a number of problems due to the removal and ejection of tissue, and these problems can lead to stroke or death. While a number of events can signal the occurrence of a steam pop, there are no available methods for providing advanced warning of an impending steam pop.

Thus, there is a need for a catheter capable of monitoring, in real-time, formation of steam pocket and thereby provide early warning of impending steam pop.

SUMMARY OF THE INVENTION

The present invention is directed to a system and method that enable real-time optical measurements of tissue reflection spectral characteristics while performing ablation. The invention involves the radiation of tissue and recapturing of light from the tissue to monitor changes in the reflected optical intensity as an indicator of steam formation in the tissue for prevention of steam pop.

In accordance with the present invention, the system includes a catheter adapted to collect light reflected from tissue undergoing ablation, a detection component that identifies and separates constituent wavelengths of collected light, a quantification apparatus for generating measured light intensity data for the collected light, and a processor that analyses the measured light intensity data in relation to time. The system may include a graphical display and/or an audio output (e.g., speaker) that provide visual and/or audio alarm when the system infers formation of a steam pocket in the tissue. In a more detailed embodiment, the processor of the system is adapted to infer the formation of a steam pocket likely to pop when it detects an initial increase in the measured light intensity and a subsequent decrease at a specified rate, and to decrease or discontinue delivery of RF energy to the ablating catheter, which may or may not be the catheter collecting light from the tissue.

The present invention is also directed to a method for monitoring formation of steam pocket during ablation, wherein a measured reflectance spectral intensity MRSI versus time is analyzed. The method includes delivering light to tissue, delivering energy for ablation at tissue and measuring the reflectance spectral intensity of the tissue, wherein observation is made as to whether the MRSI initially increases in a specified time period followed by a decrease at a specified rate in the MRSI. If there is no decrease in the MRSI, then delivery of ablation energy to tissue continues. However, if there is a decrease in the MRSI within a specified time and at a specified rate, then the method infers the formation of a steam pocket and decreases or discontinues the delivery of ablative energy to tissue.

In a more detailed embodiment, the method also determines the statistical probability of steam pop occurrence during the course of ablation. The method may also include initiating or increasing tissue cooling, such as by irrigation or infusion, to ward off steam pop if the method has inferred a specified probability of steam pop occurrence.

The present catheter and method are designed to use light in conjunction with irrigation and the technology of thermal ablation. Advantageously, the light used to monitor and assess the tissue is generally not affected by the portion(s) of the electromagnetic radiation normally used for ablation. Moreover, the wavelength region used for monitoring and assessing steam pop also transmits through blood with minimal attenuations. In addition, the use of fiber optics to emit and receive light is a generally temperature neutral process that adds little if any measurable heat to surrounding blood or tissue.

BRIEF DESCRIPTION OF THE DRAWINGS

These and other features and advantages of the present invention will be better understood by reference to the following detailed description when considered in conjunction with the accompanying drawings wherein:

FIG. 1 illustrates tissue undergoing ablation and optical monitoring in accordance with one embodiment of the present invention.

FIG. 2 is a schematic view of incidental, scattered and reflected light as occurring during optical monitoring in accordance with one embodiment of the present invention.

FIG. 3 is a schematic view of decreased reflected light and increased scattered light as occurring during formation of a steam pocket.

DETAILED DESCRIPTION OF THE INVENTION

Figure 4:
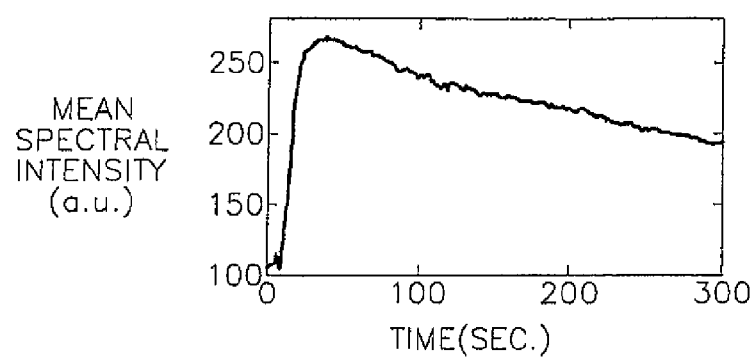
FIG. 4 is a plot of measured spectral reflection intensity of light ("MSRI") in arbitrary units (ordinate) against time in units of seconds (abscissa) measured during a lesion formation without steam pop in live canine thigh muscle.

With reference to FIG. 1, tissue 10 is subjected to RF ablation by a catheter 12. The catheter 12 has a tip section 14 adapted for ablation in creating a lesion 16 in the tissue 10. Advantageously, the catheter 12 is also adapted for optical monitoring to provide information that can tend to indicate the formation of a steam pocket in the lesion 16, particularly based on the formation of water vapor in the tissue. To that end, the catheter tip section 14 emits light that impinges on the tissue which can be reflected, scattered or absorbed. Light paths 18 impinging on the tissue and light paths 20 reflected by the tissue generally form a scattered cloud of radiation 22 inside the tissue and in the surrounding environment whose optical intensities change as a steam pocket is formed. The changes in the optical intensities include a general increase usually followed by a general decrease in the measured light intensity. In accordance with the present invention, selected characteristics of the measured light intensity curve as a function of time can provide useful data in predicting the occurrence of steam pops. This curve does not appear to be affected by the orientation of the catheter relative to the lesion. Illumination and detection need not occur in the same plane. The scattering within the tissue renders both light paths 18 and 20 to form the scattered cloud 22; thus, the present invention is functional provided the illumination and detection elements intersect the tissue-scattered cloud.

The general increase in the reflected light intensity arises from changes in the tissue during formation of a lesion which causes the tissue to be more reflective, as shown in FIG. 2. However, in instances where a steam pop may occur, the general increase in the reflected average light intensity present in the initial stages of a lesion formation by ablation may be followed by a decrease in the reflected light intensity. This decrease arises from vaporization of water in the tissue which collects in a steam pocket 24 within the tissue strata, as shown in FIG. 3. The steam pocket causes redirection 21 of the illumination light, due to the refractive index differences between the steam and the tissue. Therefore, the amount of light reflected 20 to the surface of the tissue decreases.

A catheter adapted for such optical monitoring is described in U.S. application Ser. No. 11/453,188, filed Jun. 13, 2006, and Ser. No. 11/417,092, filed May 2, 2006, the entire disclosures of which are incorporated herein by reference, although it is understood by one of ordinary skill in the art that multiple catheters may be used to deliver light to the tissue and to collect the light reflecting from the tissue.

Figure 5:
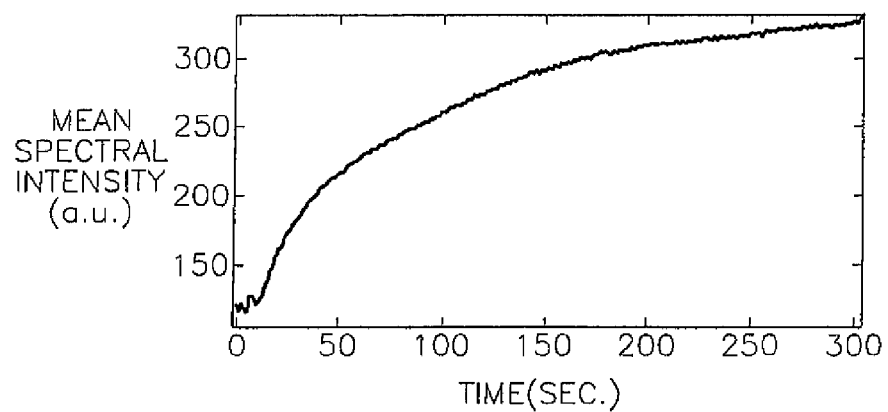
FIG. 5 is a plot of MSRI in arbitrary units (ordinate) against time in units of seconds (abscissa) measured during a lesion formation least evident to pop in live canine thigh muscle.

FIG. 4 is a plot of measured spectral reflection intensity of light ("MSRI") in arbitrary units (ordinate) against time in units of seconds (abscissa) measured during a lesion formation without steam pop collected at or near the catheter distal end shown in FIG. 1. FIG. 4 of a "non-pop" spectrum illustrates an initial increase in spectral intensity that is generally linear from time=0 to a plateau point A at about 40 secs. and then a decrease that is generally linear to about 300 secs. FIG. 5 is another "non-pop" spectrum that is of a lesion least evident to pop. Noteworthy is the gradual but steady asymptotic increase in spectral intensity from start of the ablation to finish.

Figure 7:
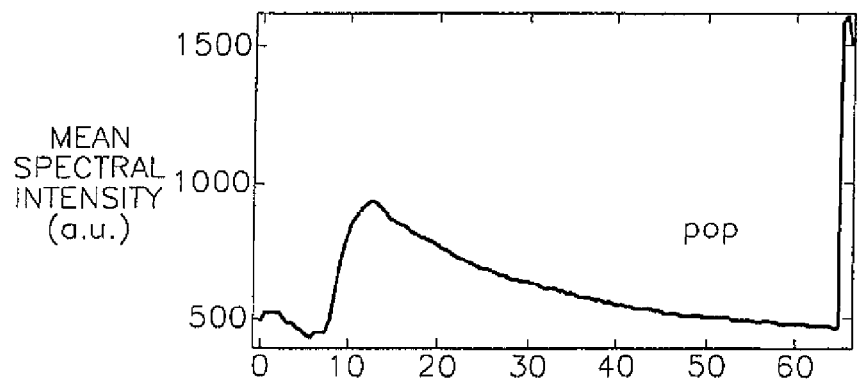
FIG. 7 is a plot of MSRI in arbitrary units (ordinate) against time in units of seconds (abscissa) measured during an ablation most evident to pop in live canine thigh muscle.
Figure 6:
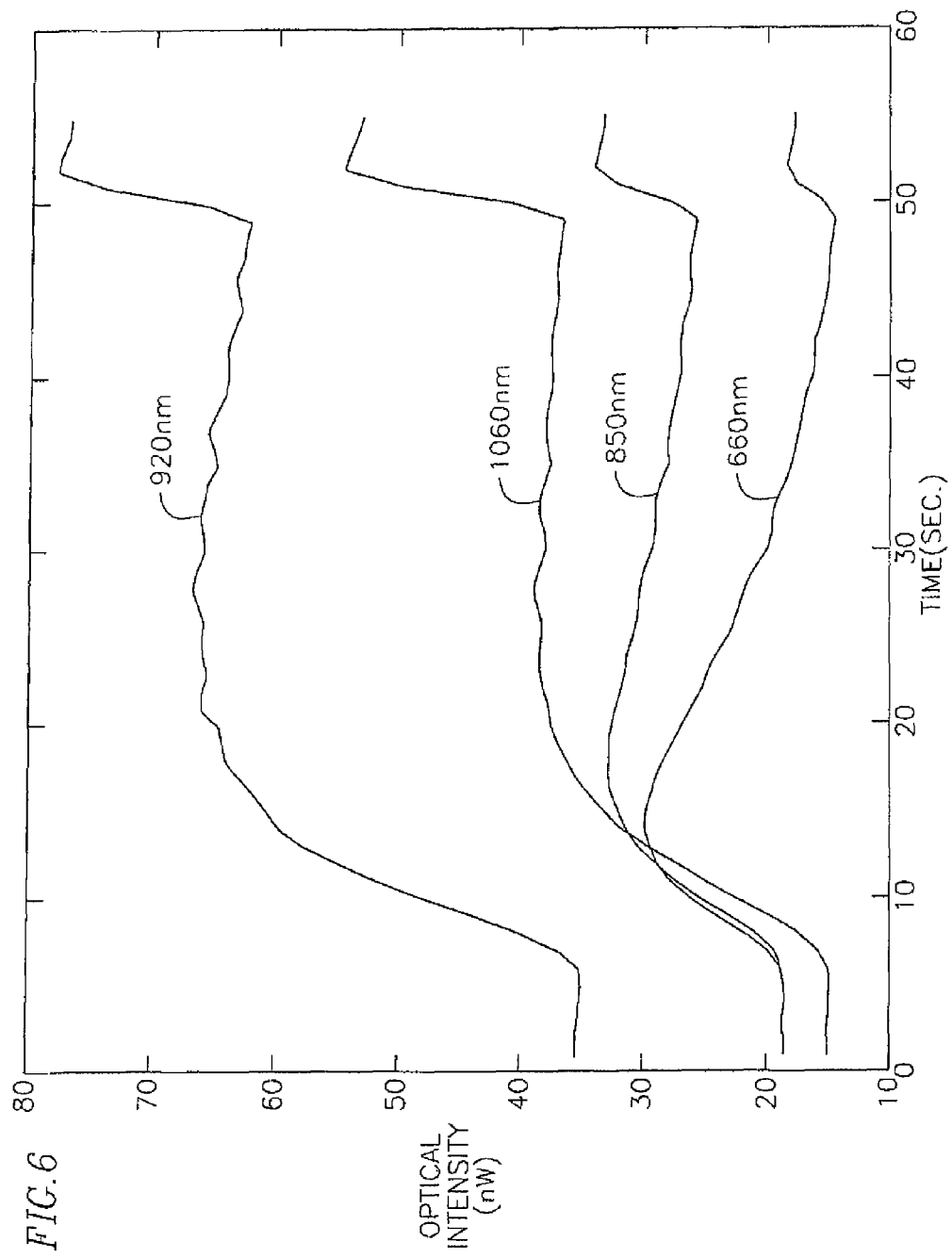
FIG. 6 a plot of representative MSRI at four different wavelengths, in nanowatts of optical power (ordinate) against time in units of seconds (abscissa) measured during ablation with steam pop in live canine thigh muscle.

In contrast, FIG. 6 is a plot of representative MSRI at four selected wavelengths, in nanowatts of optical power (ordinate) against time in units of seconds (abscissa). This figure illustrates that all of the wavelengths exhibit the same rise and fall behavior prior to pop, but the temporal location of the peak is different at each wavelength. So, although a single wavelength is all that is necessary, the method for the steam pop prediction as discussed further below varies depending on that wavelength. FIG. 7 is another "pop" spectrum that is of a lesion most evident to pop. Noteworthy is the sharp MSRI peak B at about 12 secs marking the transition from the initial increase to a relatively rapid decrease in spectral intensity.

Figure 8:
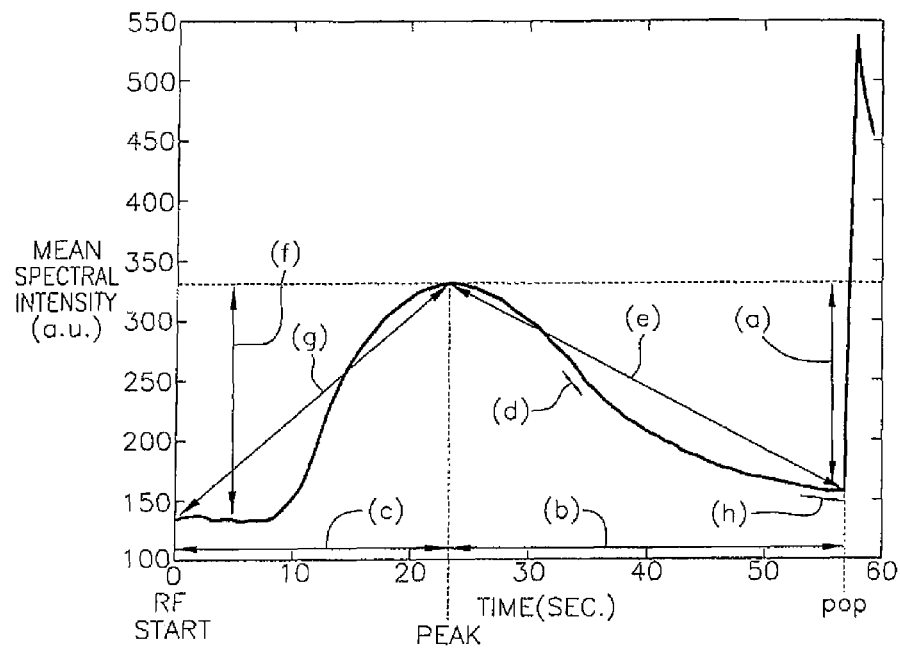
FIG. 8 is a plot of MSRI in arbitrary units (ordinate) against time in units of seconds (abscissa) measured during what could be characterized as a typical ablation session with labels corresponding to the primary descriptive components of the MSRI.

In accordance with the present invention, a typical spectrum as shown in FIG. 8 can be decomposed into various characteristic variables, including (a) percentage drop (peak to pop);
(b) time to drop or drop time (peak to pop);
(c) rise time (start to peak);
(d) maximum rate of drop (peak to pop);
(e) average rate of drop (peak to pop);
(f) percentage rise from onset (start to peak;)
(g) average rate of rise (start to peak); and
(h) last rate of drop Tissue changes due to lesion formation by RF ablation can be spectrally characterized by one or more of these eight variables or variables related thereto, such as increase and decrease in the MRSI and/or the rate of change. And, in accordance with the present invention, certain of these eight variables and/or their related variables can be monitored to provide an early indication of a potential steam pop.

Figure 9:
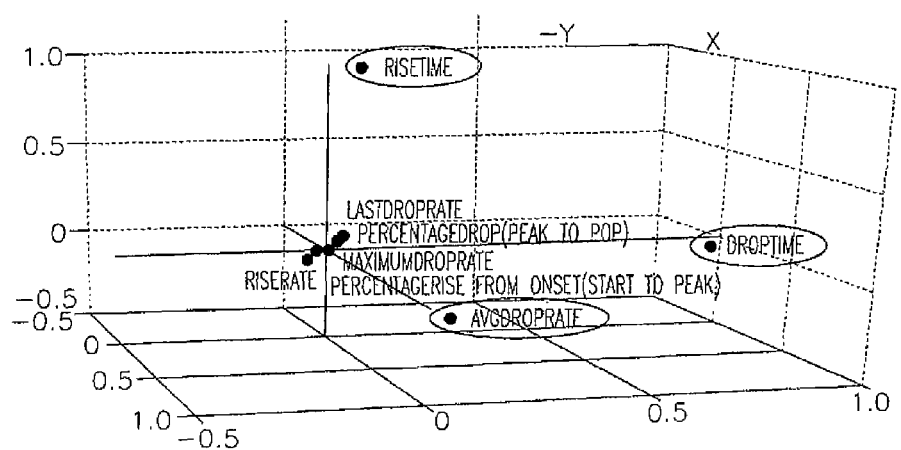
FIG. 9 shows the results of multivariate data analysis showing time-series attributes of rise time, drop time and average drop rate as most predictive of steam pop.

Using simultaneous statistical consideration of the relationships among these eight variables (or their related variables), via the application of multivariate analyses, in particular, principal component analysis (PCA) and projection to latent structures (PLS) methods, as shown in FIG. 9, the following three time-series attributes are identified with the highest correlation to steam pop prediction: (b) drop time, (c) rise time, and (e) average drop rate. Advantageously, these three attributes (and/or their related attributes) occur at such a time during lesion formation as to feasibly allow early prediction and prevention of steam pops.

In accordance with the present invention, optical spectral intensity, in particular, the measured optical spectral intensity is proficient in providing attributes and data that can be monitored to provide early warning of steam pops.

Figure 10:
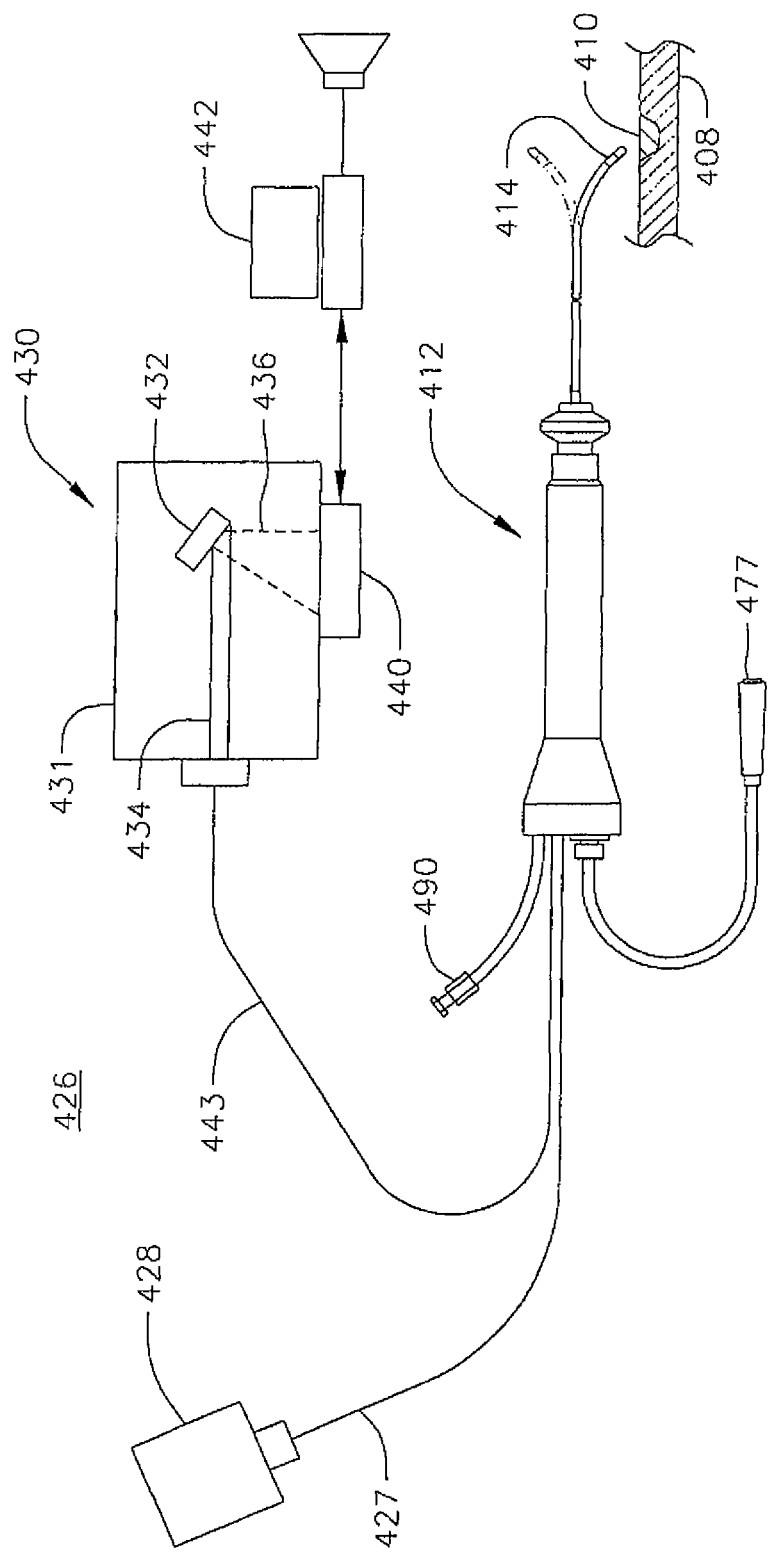
FIG. 10 is a schematic drawing showing components of an embodiment of a system of the present invention.

With reference to FIG. 10, a system 426 for monitoring lesion optical spectral intensity is shown. As understood by one of ordinary skill in the art, a catheter 412 applies ablative energy to tissue 408 to form lesion 410. In accordance with the present invention, tip section 414 of the catheter emits light that impinges on the tissue and recaptures light reflected by the tissue. The catheter 412 communicates with a patient interface unit (PIU) (not shown) via coupling 477 for ablation and other functions such as electromagnetic location sensing. Fluid may be injected by a pump (not shown) to the tissue site through a luer hub 490. The catheter 412 also communicates with an optical processing system 426. In the illustrated embodiment, the optical processing system 426 includes a light source 428 that supplies a broadband (white; multiple wavelengths) light and/or laser light (single wavelength) radiation to the tip section 414 of the catheter 412 via coupling 427. Advantageously, the present invention can be performed at any wavelength that penetrates tissue to the depth of the steam pocket. A single wavelength of light can be used or a combination of several wavelengths. Notably, the light source 428 can be a laser, blackbody radiator, diode, or any other suitable source of illumination.

Radiation can be delivered to the catheter tip section by coupling 427. Light reflected off the tissue bearing optical intensity data from the tip section 414 is transmitted to a detection component 430 via coupling 443. The detection component may comprise, for example, a wavelength selective element 431 that disperses the collected light into constituent wavelengths, and a quantification apparatus 440. The optional wavelength selective element 431 may include optics 432, as are known in the art, for example, a system of lenses, mirrors and/or prisms, for receiving incident light 434 and splitting it into desired components 436 that are transmitted into the quantification apparatus 440.

The quantification apparatus 440 translates measured light intensities into electrical signals that can be processed with a computer 442 and displayed graphically to an operator of the catheter. The quantification apparatus 440 may comprise a charged coupled device (CCD) for simultaneous detection and quantification of these light intensities. Alternatively, a number of different light sensors, including photodiodes, photomultipliers or complementary metal oxide semiconductor (CMOS) detectors may be used in place of the CCD converter. Information is transmitted from the quantification device 440 to the computer 442 that processes the information, processes the MSRI and provides a graphical display of the aforementioned time-series spectrum with at least two of the three spectral characteristics of drop time, rise time and average rate of drop (and/or their related variables). Alternately, the computer may use some combination of these spectral characteristics in an automated algorithm that provides statistical probabilities of steam pop occurrence. A suitable system for use with the catheter 10 is described in U.S. application Ser. No. 11/281179 and Ser. No. 11/281853, the entire disclosures of which are hereby incorporated by reference.

And, of the foregoing eight variables, the variables of rise time (or increase in the MRSI), drop time (or decrease in the MRSI) and average rate of drop (linearity/nonlinearity) occur at a time during ablation as to feasibly allow early prediction, if not prevention, of steam pops.

Figure 11:
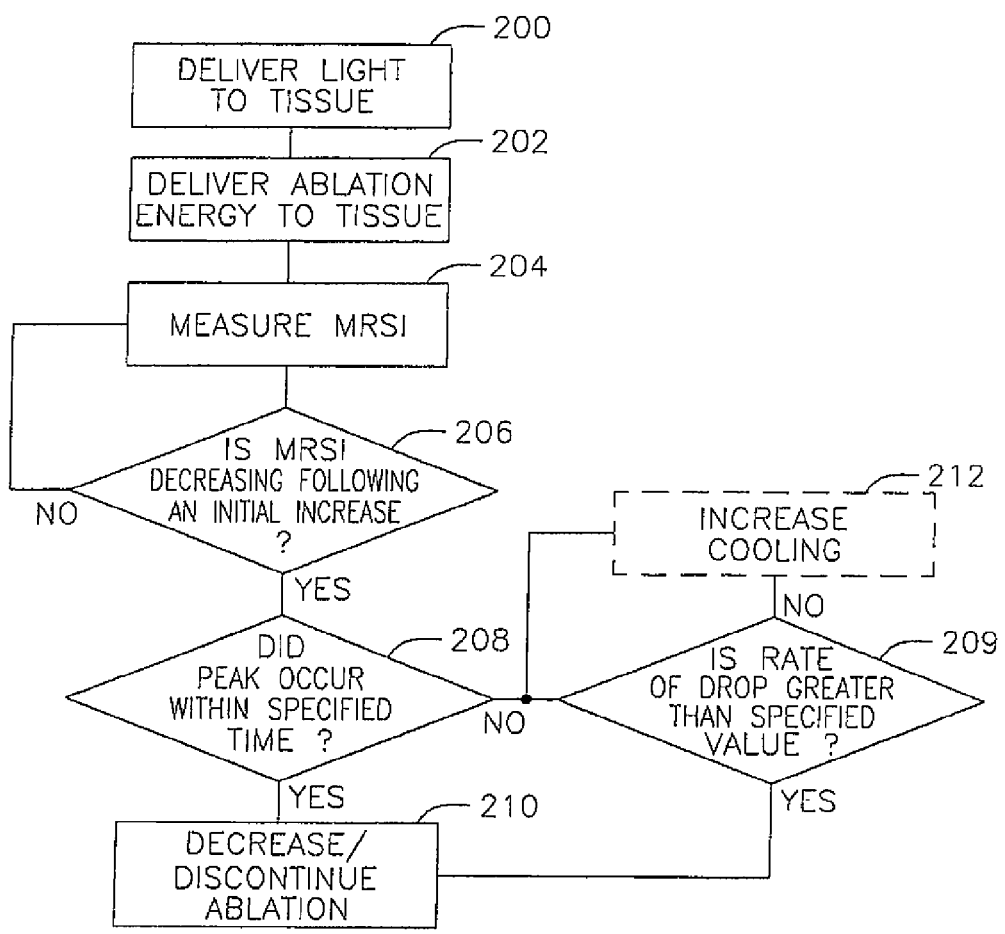
FIG. 11 is a flow chart showing a method according to one embodiment of the present invention wherein MRSI versus time is analyzed

FIG. 11 is a flowchart detailing a method according to one embodiment of the present invention wherein MRSI versus time is analyzed. The method includes delivering light to tissue (Block 200) as illustrated in FIG. 1, delivering energy for ablation at tissue (Block 202) to form lesion and measuring intensity of light reflected off tissue (Block 204). Initial analysis of the MRSI versus time determines if the MRSI has decreased following an initial increase, or peaked (Decision Block 206). If the MRSI has not peaked, then delivery of ablation energy to tissue continues (Block 202). However, if the MRSI has peaked, a next analysis is performed determining if the peak occurred within a specified time period (Decision Block 208). If the MRSI has peaked within a predetermined or specified amount of time, then the method infers an impending steam pop and discontinues the ablation (Block 210). If the peak occurred after a predetermined or specified amount of time, the rate of drop is continuously monitored (Decision Block 209). If the rate of drop exceeds a specified amount, then the method infers an impending steam pop and discontinues ablation (Block 210). If the rate of drop does not exceed the specified amount, then delivery of ablation energy continues. As mentioned above in relation to FIG. 6, because the temporal location of the MRSI peak is different at each wavelength, the specified amount of time and/or the specified amount of the rate of Decisions Blocks 208 and 209 varies depending on the wavelength used in the present invention.

In the method of FIG. 11, this method may include initiating or increasing cooling of the tissue (Block 212) where the method has not yet inferred the formation of a steam pop but is approaching such an inference. As understood by one of ordinary skill in the art, cooling of tissue may include irrigation, infusion or heat exchange.

The spectral window through blood is between about 600 nm and 2000 nm, with some spots of absorption in between. A preferred range is between about 650 nm and 1300 nm, although different wavelengths, particularly monochromatic light sources, may not produce the same MSRI. that is, the intensity peak and the various slopes and drops are not the same for the same steam pop. When using only a single wavelength, the present invention may perform with better sensitivity and specificity; however, any single wavelength may not clearly outperform any other single wavelength. A more preferred wavelength may be about 900 nm.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Accordingly, the foregoing description should not be read as pertaining only to the precise structures described and illustrated in the accompanying drawings, but rather should be read consistent with and as support to the following claims which are to have their fullest and fair scope.

What is claimed is:

1. A method of predicting formation of steam pops in tissue during ablation over a period of time, comprising:
    delivering light onto the tissue during the ablation;
    observing a measured reflectance spectral intensity (MRSI) versus time of the tissue during the ablation, wherein an observation is made as to at least:
    an initial increase in the MRSI;
    a subsequent decrease in the MRSI; and
    one of a group consisting of a peak and a plateau in the MRSI, between the initial increase and the subsequent decrease in the MRSI; and
    predicting formation of a steam pop prior to formation of any steam pop based on the observation.

2. The method of claim 1, further comprising continuing or discontinuing the delivering light onto the tissue to prevent formation of any steam pop in response to the predicting.

3. The method of claim 1, wherein the initial increase has a first generally linear rate and the subsequent decrease has a second generally linear rate.

4. The method of claim 3, wherein the first generally linear rate has a greater slope and the second generally linear rate has a lesser slope.

5. The method of claim 1, wherein the observation includes observing the plateau at about 40 seconds after start of ablation.

6. The method of claim 5, further comprising continuing the delivering light onto the tissue in response to the observation of the plateau.

7. The method of claim 1, wherein the observation includes observing the peak after start of ablation.

8. The method of claim 7, further comprising discontinuing the delivering light onto the tissue in response to the observation of the peak.

9. A method of predicting no formation of steam pops in tissue during ablation over a period of time, comprising:
   delivering light onto the tissue during the ablation;
   observing a measured reflectance spectral intensity (MRSI) versus time of the tissue during the ablation, wherein an observation is made as to at least a gradual but steady asymptotic increase in MRSI from start of ablation to finish; and
   predicting no formation of steam pop prior to formation of any steam pop based on the observation.

10. A method of predicting formation of steam pops in tissue during ablation during a period of time, comprising:
    delivering light onto the tissue during the period of time;
    observing a measured reflectance spectral intensity (MRSI) versus time of the tissue during ablation, wherein observation is made as to:
    an increase in the MRSI;
    a decrease in the MRSI; and
    a peak in the MRSI within a duration of time from start of ablation between the increase and the decrease in MRSI; and
    discontinuing the delivering light onto the tissue to prevent formation of any steam pop in response to the observation.

11. The method of claim 10, wherein the discontinuing the delivering light occurs within about 60 seconds or less after start of ablation.

12. The method of claim 10, wherein the observation is also made as to a rise time in which MRSI reaches a peak.

13. The method of claim 10, wherein the observation is also made as to a drop time in which MRSI drops from the peak to a threshold steam pop formation value.

14. The method of claim 10, wherein the observation is also made as to an average drop rate of the MRSI.

* * * * *